United States Patent
Mosebach et al.

(10) Patent No.: US 10,832,553 B2
(45) Date of Patent: Nov. 10, 2020

(54) SYSTEM FOR ALERTING A PERSON

(71) Applicant: Vorwerk & Co. Interholding GmbH, Wuppertal (DE)

(72) Inventors: Andrej Mosebach, Bochum (DE); Christian Holz, Dortmund (DE)

(73) Assignee: Vorwerk & Co. Interholding GmbH (DE)

( * ) Notice: Subject to any disclaimer, the term of this patent is extended or adjusted under 35 U.S.C. 154(b) by 13 days.

(21) Appl. No.: 16/263,925

(22) Filed: Jan. 31, 2019

(65) Prior Publication Data

US 2019/0236925 A1    Aug. 1, 2019

(30) Foreign Application Priority Data

Feb. 1, 2018 (EP) .................................. 18154690

(51) Int. Cl.

| G08B 21/00 | (2006.01) |
|---|---|
| G08B 21/04 | (2006.01) |
| G08B 21/06 | (2006.01) |
| G08B 6/00 | (2006.01) |
| G08B 21/18 | (2006.01) |
| G16H 40/20 | (2018.01) |
| G16H 40/67 | (2018.01) |

(52) U.S. Cl.
CPC .......... *G08B 21/0453* (2013.01); *G08B 6/00* (2013.01); *G08B 21/043* (2013.01); *G08B 21/06* (2013.01); *G08B 21/182* (2013.01); *G16H 40/20* (2018.01); *G16H 40/67* (2018.01)

(58) Field of Classification Search
CPC .. G08B 21/0453; G08B 21/043; G08B 21/06; G08B 21/182; G16H 40/20; G06H 40/67
USPC .................................................. 340/426, 573.1
See application file for complete search history.

(56) References Cited

U.S. PATENT DOCUMENTS

| 8,753,273 | B1 * | 6/2014 | Lau | G06F 11/3013 600/300 |
|---|---|---|---|---|
| 2004/0027246 | A1 * | 2/2004 | Aguglia | A61B 5/0002 340/573.1 |
| 2008/0266118 | A1 * | 10/2008 | Pierson | A61B 5/0205 340/573.6 |
| 2010/0022848 | A1 * | 1/2010 | Lee | A61B 5/0002 600/300 |
| 2015/0351698 | A1 * | 12/2015 | Cronin | A61B 5/0022 600/485 |
| 2016/0035205 | A1 | 2/2016 | Messenger et al. | |

* cited by examiner

*Primary Examiner* — Ojiako K Nwugo
(74) *Attorney, Agent, or Firm* — Barnes & Thornburg LLP

(57) ABSTRACT

The present disclosure concerns a system comprising an evaluation unit 1 that allows to determine an occurrence of an event and, when the event occurs, to alert a plurality of persons 2, 3 and/or to inform them about the occurred event. The system comprises for each person 2, 3 a control unit 6, 7 and a sensor 8, 9. The control unit 6, 7 can be connected to the evaluation unit 1 for exchanging data. The sensor 8, 9 can measure a vital parameter of the respective person 2, 3. The system is configured such that when the evaluation unit 1 determines the occurrence of an event, at least one person 3 of the plurality of persons 2, 3 is selected based on the measured vital parameters and only the at least one selected person 3 can be alerted. The present disclosure furthermore concerns a use, a method and a computer program product. The Stress caused by the alerting can thereby in all be reduced.

20 Claims, 1 Drawing Sheet

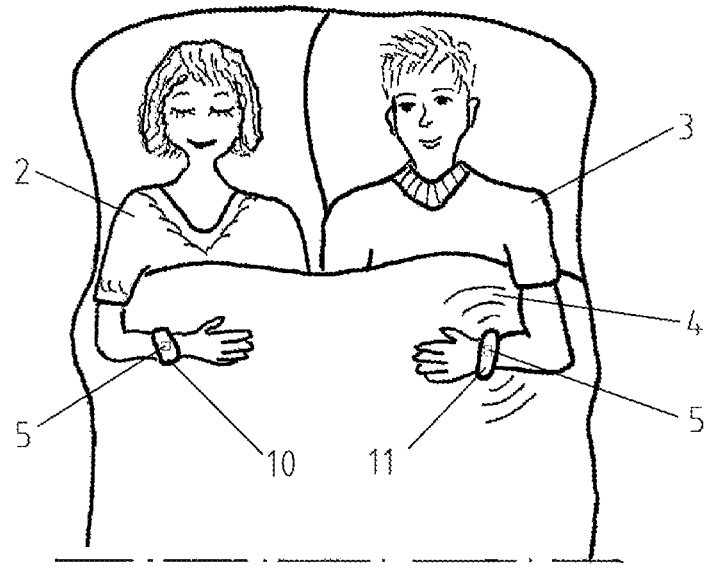
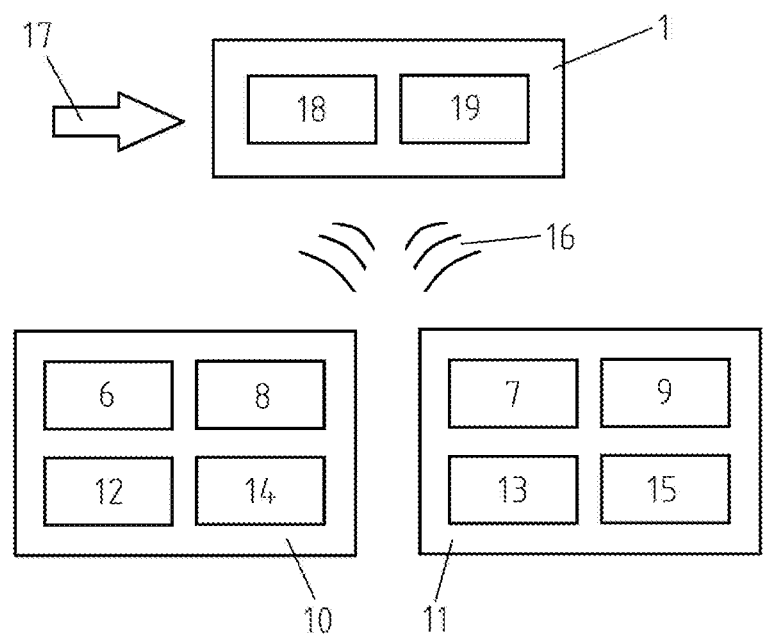

… (1)

SYSTEM FOR ALERTING A PERSON

PRIORITY CLAIM

This application claims priority to European Application No. 18 154690.4, filed Feb. 1, 2018, which application is hereby incorporated in its entirety herein.

FIELD OF THE DISCLOSURE

The present disclosure concerns a system comprising an evaluation unit that allows to determine an occurrence of an event and, when the event occurs, to alert a plurality of persons and/or to inform them about the occurred event.

BACKGROUND

In infant care as well as elderly care there are systems in which, for example, an audio baby monitor or a mobile emergency call button can be used to inform and/or alert one or more supervisors. In particular, the nightly alerting of a sleeping supervisor, which is awakened by the alerting, reduces the nightly recovery. The document US2016/035205A1 discloses a system, in which only one parent of two parents is alerted such that the other parent is not awoke and sleeps on.

It is object of the present disclosure to provide a further developed system.

SUMMARY

For solving the problem, a system, a method, as well as a computer program product according to the independent claims are provided. Preferred embodiments are described in the subclaims.

To solve the problem, a system comprising an evaluation unit is provided that allows to determine an occurrence of an event and, when (upon) the event occurs, to alert a plurality of persons and/or to inform them about the occurred event. The system provides for each person a control unit and a sensor. The control unit can be connected to the evaluation unit for exchanging data. The sensor can measure a vital parameter of the respective person. The system is configured such that when the evaluation unit determines the occurrence of an event, at least one person of the plurality of persons is selected based on the measured vital parameters and only the at least one selected person can be alerted.

The stress caused by alerting can thus be reduced for the persons as a whole, i.e. in total. On the one hand, the overall stress can already be reduced by simply making a selection of persons, because this allows not to necessarily alerting all possible persons.

On the other hand, the selection of persons based on the measured vital parameters enables that as little stress as possible is caused in the selected and alerted person, especially in comparison to at least one other person in the plurality of persons.

Vital parameter means a state variable of an organism of a living person, which can generally be indicated by a measured value. As a rule, a vital parameter describes a basic function or vital function. A vital parameter, i.e. the measured value, can be determined using a sensor. Heart rate, blood pressure, body temperature or respiratory rate are examples of vital parameters.

Based on a measured vital parameter such as blood pressure, it is possible to determine whether a person is currently in a particularly tense situation. For a person in a tense situation, alerting causes increased stress compared to a person who is not in a tense or less tense situation at the moment.

On the basis of a measured vital parameter such as pulse rate, it is possible to determine whether a person is currently engaged in physically strenuous activity such as sports or strenuous housework. Such a person is normally busy and alerting would cause increased stress compared to a person who is not engaged in strenuous activity.

On the basis of a measured vital parameter such as movement activity or electrical voltage fluctuations on the scalp surface, it is in one embodiment possible to determine whether a person is currently in a particularly deep sleep phase. For a person in a particularly deep sleep phase, alerting causes increased stress compared to a person who is currently in a sleep phase with little sleep depth.

Alerting means that a person is exposed to a stimulus that the person notices. The person should thereby be caused to take notice of the reason for the alert and/or to carry out a certain action. The reason for the alert may be an event that has just occurred. When the event occurs, at least one person is thus alerted. The alerting is then sufficient so that the person is taking notice of the occurrence of the event. An alert is in one embodiment arranged in such a way that even a person in deep sleep is awakened by the alert and can take notice of the reason for the alert. The stimulus can be in one embodiment a targeted movement such as pressing, pushing, pulling or vibrating. The stimulus can, in an alternative or complementary embodiment, be an acoustic signal or a stimulus induced by current.

An information can be, in one embodiment, made available in a digitally retrievable form, e.g. on a smartphone or through an app, i.e. application software, of a smartphone, in order to provide an information in the claimed manner. An information can, in one embodiment, be displayed on a display. However, unlike alerting, informing does not primarily aim at ensuring that the informed person takes notice of the information immediately at the time the information is made available. For example, a deeply asleep person is not awakened by way of informing. In general, all persons are always informed when an event occurs.

An event within the meaning of the present disclosure has been defined beforehand. The event is stored in the evaluation unit. In one embodiment, several different events are stored in the evaluation unit.

If an event occurs, the evaluation unit recognizes that the event has occurred. If several events are stored, the evaluation unit also recognizes which event has occurred.

In one embodiment, the event is an incoming telephone call. The evaluation unit can then select a person based on the measured vital parameters and forward the call to, for example, the mobile phone or smartphone of this selected person.

In one embodiment, the event is an incoming emergency service request, in particular for persons on standby duty such as a group of medical doctors in the hospital or a team of firefighters in the fire station. Based on the measured vital parameters, the evaluation unit can then select a person or a needed number of persons to be alerted to accept the emergency service request.

In one embodiment, the event is a message from a monitoring device such as a burglar alarm system or an audio baby monitor. The evaluation unit can then, based on the measured vital parameters, select and alert a person, e.g. a parent, to take notice of the message.

The expression "based on the measured vital parameters" means that one vital parameter per person is measured for the selection of the at least one person, and the vital parameters measured in this way are evaluated by the evaluation unit. In particular, the evaluation unit compares the measured vital parameters of the individual persons with each other. Alternatively or additionally, the measured vital parameters of the individual persons are compared with a defined threshold for alerting.

If the evaluation based on the measured vital parameters shows that all persons are suitable for alerting, all persons of the plurality of persons can be selected and alerted. The "only the at least one selected person" are then all persons of the plurality of persons. This reduces the risk that an alerted person has not taken notice of the alert, for example due to a technical defect.

The "plurality of persons" includes every person with an own sensor and control unit. The sensor can measure the vital parameter of the person and transmit a corresponding sensor signal to the control unit. The control unit can in turn transmit a measurement signal that corresponds to the sensor signal to the evaluation unit. In the simplest case, the control unit is a data interface. A sensor signal is in particular an analog signal, whose voltage, current and/or frequency correlates with the measured vital parameter, i.e. its measured value. In one embodiment, the control unit carries out signal processing of the sensor signal, i.e. signal conversion and/or signal modification. Preferably, the control unit performs an analog-to-digital conversion and/or a signal modification through an algorithm. The measurement signal transmitted from the control unit to the evaluation unit is preferably digital and/or corresponds to the measured value of the vital parameter.

In one complementary embodiment, several vital parameters are measured, i.e. several different vital parameters. A suitable person or several suitable persons can thus be selected particularly reliably for the alerting.

An evaluation unit preferably comprises a processor and a memory with a computer program code, i.e. commands (instructions) that are storable in the memory. The processor, the memory and the computer program code are configured in such a way that a method with several method steps can be executed. By means of method steps, at least one person can be selected for the alerting in a way according to the present disclosure.

Preferably, a selection is conducted using an algorithm that is reflected in a computer program code and/or can be executed through method steps. In particular, the control unit also includes a processor and a memory with a computer program code.

In one embodiment, the system provides an alert unit for each person, which is arranged such that only the respective person can be alerted by the alert unit. When the alert unit is activated for alerting a person, only the person to whom the alert unit is assigned to is thus alerted in a targeted manner. When the person is alerted, another person is thus not alerted.

Cases, in which another person perceives the alert for the person by chance or incidentally, are excluded from this consideration. If, for example, the alert is realized by vibration, only the person feels the vibration, e.g. through direct skin contact with the alert unit. If another person only perceives the vibration acoustically, this other person is not alerted within the meaning applied herein.

An alert unit that only alerts the respective person allows other persons to remain undisturbed when the event occurs, even if the other person or persons are in the vicinity of the alerted person.

By this way, not alerted medical doctors, firefighters or parent(s) for example can continue to sleep while the alerted colleague or parent (spouse) is awakened by the alert and takes appropriate action in response to the event.

When the evaluation unit determines the occurrence of an event, only the alert unit of the selected person or the alert units of the selected persons are activated for alerting.

In one embodiment, the system provides a display for each person in order to display an information about the occurred event. The alerted person can thereby receive detailed information about the event or find out which of several possible events has occurred. The alerted person can also receive action instructions via the display.

Any non-alerted person can also view the information about the event through the display assigned to him/her at an appropriate time. In this way, every person can be informed without having to be alerted.

In one embodiment, the control unit and the sensor are integrated in a receiving device, which is intended to be carried by the respective person. The receiving device is thus uniquely assigned to only one person of the plurality of persons. The receiving device reduces the number of parts and thus increases the comfort of use.

In particular, the evaluation unit and the receiving device, preferably the control unit of the receiving device, have a WLAN interface and/or an internet interface. The risk of failure of data transmission due to movements and, for example, cable breakage can thus be avoided.

In one embodiment, the alert unit and/or the display are integrated in the receiving device. The receiving device thus further reduces the number of parts.

In one embodiment, the receiving device has a fastening means for fastening to the body of a person and/or comprises a skin-compatible contact surface for direct fastening to the body. Thanks to the fastener, the receiving device can be carried on the body so that the person can always be reliably alerted.

The skin-compatible contact surface enables to use a sensor that can measure a vital parameter through direct skin contact, like for example the body temperature or electrical voltage fluctuations on the skin surface. Various vital parameters can thus be measured particularly reliably.

The skin-compatible contact surface enables the use an alert unit that exerts a stimulus directly on the skin surface, like for example vibration, pressure or an electrical stimulus. This makes it possible to alert in a particularly targeted manner, i.e. without alerting another person.

In one embodiment, the receiving device is a bracelet (wristband), a footband or a headband. The receiving device thus comprises in particular textile components which give the receiving device the external appearance and function of a bracelet, a footband or a headband. Alternatively, the receiving device may be integrated into a bracelet, footband or headband. A bracelet, footband or headband allows the receiving device to be worn reliably on the body, particularly under permanent skin contact. A sensor that requires direct skin contact to measure a vital parameter can thus be used particularly reliably. At the same time, alerting thus be performed in a particularly targeted manner by an alert unit, which is arranged to directly exert a stimulus on the skin surface.

In one embodiment, the sensor and/or the alert unit are arranged for direct skin contact. Hence, in a ready-to-operate status, the sensor and/or the alert unit are in direct contact with a skin surface. It can thus be measured or alerted particularly reliably and in various ways.

In one embodiment, the alert unit is a vibration generator. By means of a vibration generator, a person can be alerted in a targeted manner without alerting another person in the vicinity in a comparable way. The vibration generator is preferably placed with a skin-compatible contact surface directly on the skin surface of the person. A vibration generator generates a mechanical vibration preferably by means of a rotating unbalance. A vibration generator generates a vibration in a frequency range of generally at least 20 Hz.

In one embodiment, the sensor is a gyrometer. In particular, a gyrometer is used to measure a rotational movement. By measuring the rotational movement, a measure of activity can be determined as a vital parameter of the person. In particular, a change of direction of a rotational movement is detected and/or a number of changes of direction per time interval of e.g. ten seconds is determined. If, for example, at least six changes of direction take place in a ten-second period, this is an indication of a waking state. If no change of direction is detected within a time interval, the person is in a deep sleep phase or at least a relatively deep sleep phase. In particular, the rotational movement is measured at the wrist. A particularly reliable determination of the activity can thus be enabled. Alternatively or additionally, the gyrometer can be used to determine an acceleration. Alternatively or additionally to the gyrometer, it can be used a force sensor, a force transducer, a piezo sensor and/or a strain gauge.

In particular, the at least one sensor can be a moisture sensor e.g. for detecting sweat discharge e.g. to determine physical exertion, a motion sensor mat to determine activity, a pulse monitor e.g. to determine physical exertion, a blood pressure meter e.g. to determine mental tension, a brain current sensor for EEG and/or ECG e.g. to determine the activity of the body, an oxygen measuring sensor e.g. to determine a sleep phase, a camera e.g. to determine the activity, a blood sugar level sensor, a $CO_2$ measuring device for breathing air, a pupil size measuring device, a blinking frequency measuring device and/or a breathing frequency measuring device.

In one embodiment, the evaluation unit compares the measured vital parameters of the individual persons with each other in order to select the at least one person. The person most suitable for the alert is then selected in comparison to the other person or persons based on the measured vital parameter or the measured different vital parameters. In particular, one or more criteria are stored for this evaluation.

In one embodiment, one criterion defines to alert the person with the least tension. Blood pressure, pulse frequency and/or activity can be used as the vital parameter. Preferably, a determined waking state can be a prerequisite for this criterion. In this embodiment, the criterion is used to select the awake person who appears to be the least busy one. The stress caused by the alerting of an awake person can thus be minimized altogether.

In an alternative or complementary embodiment, another criterion defines to select the person among sleeping persons who is in a sleep phase with the least depth of sleep. The activity or electrical voltage on the scalp surface can be used as vital parameter. The stress caused by the alert in a sleeping person can thus be minimized altogether.

In one embodiment, the evaluation unit compares the measured vital parameters with a threshold in order to select the at least one person. Several suitable persons can thereby be selected particularly easily. In particular, all persons whose measured vital parameter reaches a threshold or is above a threshold are selected. If the vital parameter is the activity of a sleeping person, then all persons can be selected in this way who are currently in a sleep phase with a predefined low sleep depth. Alternatively or additionally, all persons can be selected whose measured vital parameter is below a threshold. All persons who are, based on blood pressure and/or pulse frequency, under such predefined, relatively low tension or exertion can thus be determined and selected particularly easily.

In one embodiment, a minimum number of persons to be selected and/or a maximum number of persons to be selected is defined.

In particular, the comparison of the measured vital parameters of the plurality of persons as well as the comparison of a measured vital parameter of a person can be considered jointly by the evaluation unit. A particularly reliable selection of at least one person can thus be made possible, particularly with a fixed minimum number and/or maximum number of persons to be selected.

In one embodiment, the evaluation unit is equipped with a machine learning algorithm for selecting the at least one person. Based on the input variables in form of the measurement signals of the control units of the individual persons of the plurality of persons, the evaluation unit can select as output variable the at least one person particularly suitable for alerting, in particular if several different vital parameters are provided.

A machine learning algorithm generally assigns an output variable to one or more input variables. The output variable can also be a data set with several selected persons. A machine learning algorithm is often the basis for so-called "artificial intelligence", whereby the machine learning algorithm "learns" from experience and "recognizes" patterns and laws independently even in unknown data. A machine learning algorithm can be formed by a so-called "neural network" or comprise a "neural network" in the form of a corresponding program. In particular, a machine learning algorithm is generated by a modelling phase and a subsequent identification phase in order to be able to forecast a (point in) time for the occurrence of a state change in an application phase. In particular, the modelling phase takes place at the manufacturer's site. The identification phase can take place at the manufacturer and/or at the end user. The application phase then takes place at the end user. For test purposes, the application phase can take place at the manufacturer.

In the modelling phase, a mathematical model, i.e. a system of equations, is created to assign one or more input variables to an output variable. A relationship between one or more vital parameters and the selection of the corresponding person is taken into account, i.e. reflected in the mathematical equation system. Preferably, a dynamic model and/or differential equation system for the selection of at least one person based on the measured vital parameters is created in the model building phase. In the model or differential equation system, the measured vital parameters or the corresponding measurement signals of a defined sensor or several defined sensors serve as input variable or input variables and the selection of the person or persons the output variable.

In the identification phase, the machine learning algorithm is supplied with a plurality of value pairs each with an input variable and an output variable or with several input variables and one output variable respectively. In this way, the machine learning algorithm is optimized and adapted to reality. In particular, constants are optimized in a differential equation system of the machine learning algorithm based on the supplied value pairs. By providing a user interface that allows the user to input feedback, an output variable can be supplied to the machine learning algorithm. The user can input feedback using an app, a smartphone, a tablet PC and/or another feedback unit connected to the evaluation unit.

In the application phase, the machine learning algorithm is used to select, based on the measurement signals, the at least one person who is then alerted in the manner described above.

By equipping the evaluation unit with the machine learning algorithm, it is possible to select the at least one person with particular precision. It is possible to generalize and derive regularities from the course of one or more vital parameters of individual persons, alone as well as in comparison with each other. An application which takes into account the peculiarities of the respective person and/or the plurality of persons as a whole can thus be achieved.

A further aspect of the present disclosure concerns the use of the system according to the aspect of the present disclosure as described at the beginning, wherein the event is an awakening of an infant and the plurality of persons are the two parents. In particular, the use is carried out at night and/or during the normal sleep and/or resting period of the two parents. Thus, when the infant wakes up at night, the system allows to only wake up the parent who is in a sleep phase with less depth compared to the other parent.

A further aspect of the present disclosure concerns a system, in particular according to the aspect of the present disclosure as described at the beginning, comprising an evaluation unit that allows to determine an occurrence of an event and, when the event occurs, to alert a plurality of persons and/or to inform them about the occurred event. The system provides for each person a control unit and a sensor. The control unit can be connected to the evaluation unit for exchanging data. The sensor can measure a vital parameter of the respective person. When the evaluation unit determines the occurrence of an event, at least one person of the plurality of persons is selected based on the measured vital parameters and only the at least one selected person is alerted.

A further aspect of the present disclosure concerns a method in which a vital parameter of an organism is measured and a measurement signal corresponding thereto is output. An evaluation unit evaluates the measurement signal and forecasts a (point in) time of the occurrence of a change of condition of the organism based on the evaluated measurement signal. The features, embodiments and effects of the system to solve the problem as described at the beginning are also, in analogy to that, related to this method.

A further aspect of the present disclosure concerns a computer program product. The computer program product comprises instructions (commands) which, when the program is executed by a computer, cause the computer to execute the steps of the method according to the preceding aspect of the present disclosure. In particular, the computer is the evaluation unit. The features, embodiments and effects of the system to solve the problem as described at the beginning are also, in analogy to that, related to this computer program product.

In the following, embodiment examples of the present disclosure are explained in more detail also using figures. Features of the embodiment examples and further alternative or supplementary embodiment described below can be combined individually or in a plurality with the claimed objects. The claimed scope of protection is not limited to the embodiment examples.

BRIEF DESCRIPTIONS OF THE DRAWINGS

It is shown:

FIG. 1: Schematic illustration of an exemplary application of a system for alerting a selected person of a plurality of persons when the occurrence of an event is determined;

FIG. 2: Schematic overview of the components of a system for alerting and their exemplary structure.

DETAILED DESCRIPTION

FIG. 1 shows a person 2 and another person 3 particularly during a resting phase for example at night. Both persons 2, 3 carry (wear) a receiving device 10, 11 each in form of a bracelet. Each of the persons 2, 3 is informed when an event occurs. For this purpose, an information 5 is displayed. However, only the selected person 3 is additionally alerted by an alert signal 5 when an event occurs, so that the person 3 is promptly taking notice of the occurrence of the event.

FIG. 2 shows the structure of a system for alerting comprising an evaluation unit 1 and several receiving devices 10, 11. In particular, it is the system of FIG. 1. Each receiving device 10, 11 comprises a display 14, 15 and/or an alert unit 12, 13. The displays 14, 15 can display an information 5 about the occurred event. The activated alert unit 13 of the selected person 3 gives an alert signal 5 in the form of a vibration for altering to the person 3 who gets woken up by it. Person 2, on the other hand, is not woken up by the alert signal 5.

Each receiving device 10, 11 comprises a sensor 8, 9 for measuring a vital parameter of the respective person 2, 3. The term "respective person" refers to the person carrying (wearing) the receiving device 10, 11 and thus is assigned to this receiving device 10, 11.

Each receiving device 10, 11 comprises a control unit 6, 7. The control unit 6, 7 is connected to the evaluation unit 1 for exchanging data. The connection is in particular a wireless connection. A radio connection or WLAN connection is preferably used as the wireless connection.

The evaluation unit 1 comprises a processor 18 and a memory 19. A computer program, respectively computer program product, is stored on the memory 19 by which an input signal 17 can be evaluated for determining the occurrence of an event. In one embodiment, it is provided only one event whose occurrence can be determined by the evaluation unit 1. Computing capacity can thereby be saved. In one preferred embodiment, several different events are provided whose respective occurrence can be determined by the evaluation unit 1.

The sensor 8, 9 measures a vital parameter of the person 2, 3 and transmits a corresponding sensor signal to the control unit 6, 7.

In one embodiment, the control unit 6, 7 performs a signal processing of the sensor signal in order to obtain a measurement signal 16 for the evaluation unit 1. Alternatively or additionally, the control unit 6, 7 forwards the sensor signal to the evaluation unit 1.

In one embodiment, the control unit 6, 7 transmits the processed measurement signal 16 to the evaluation unit 1, in particular together with an assignment to the person 2, 3 or to the receiving device 10, 11 of the person 2, 3, whose vital parameters are described by the measurement signal 16.

In one embodiment, the control unit 6, 7 evaluates the sensor signals in such a way that the measurement signal 16 already indicates whether the person 2, 3 is to be selected or not. The evaluation unit 1 can thus be relieved. In one embodiment, the control unit 6, 7 records the sensor signals over a predefined period of time in order to carry out signal processing and/or evaluation. This enables particularly reliable and high-quality signal processing and evaluation. In one embodiment, the evaluation unit 1 is configured to record the measurement signals 16 for evaluation over a predefined period of time. A particularly reliable selection of the at least one person 3 can thus be achieved.

In one embodiment, the evaluation unit 1 triggers the measurement of a vital parameter by the sensor 8, 9 and/or the transmission of the measurement signal 16 to the evaluation unit 1. Unnecessary measuring, processing and transmission procedures can thus be saved.

When the evaluation unit 1 has determined, thus detected, the occurrence of an event, an evaluation of the measurement signals 16 of the individual persons 2, 3 is carried out in order to select at least one person 3 for alerting.

In a first example, the input signal 17 is an incoming call. The evaluation unit 1 then requests a current measurement signal 16 from the receiving devices 10, 11 of the plurality of persons 2, 3. By means of thresholds that are stored in the evaluation unit 1, i.e. saved in memory 19, at least one of the persons 2, 3 is selected for alerting. For example, the vital parameter is the activity. The measurement signals 16 have shown that person 2 sleeps deeper than the further person 3. At the same time, the sleep depth of person 2 is below a threshold for a selection or alert, respectively. Therefore, the evaluation unit 1 sends an information about the incoming call, e.g. the telephone number of the caller and the receiving time of the call, to the receiving devices 10, 11 of both persons 2, 3, so that the information can be displayed or retrieved on the displays 14, 15. A control signal for activating the alert unit 12, 13 is only provided to the receiving device 11 of the further person 3. The alert unit 13 of the further person 3 particularly emits a vibrating alert, which preferably acts directly on the skin surface of the further person 3. By this way, the further person 3 gets woken up while the person 2 continues to sleep and is not woken up by the alerting of the further person 3. The further person 3 will then go to the telephone and answer the call. In one embodiment, the evaluation unit 1 forwards the call directly to the (his) mobile phone or smartphone or the (his) receiving device 11 with telephone function.

In a second example, the input signal 17 indicates that an infant has woken up or will wake up after a forecasted time period as passed. In particular, the infant has a sensor installation for detecting a vital parameter of the infant, which is connected to an analysis installation. In particular, based on the measured vital parameter, the analysis installation allows to determining or forecasting the awakening of the infant, preferably by means of a machine learning algorithm.

When the evaluation unit 1 determines the occurrence of the awakening or a forecasted awakening of the infant based on the input signal 17, at least one person 3 is, based on the vital parameters of the plurality of persons 2, 3 measured by the sensors 8, 9, selected and alerted by the receiving device 11. Then one person 3, in particular only one parent, needs to take care of the infant only. The resting period for parents of an infant can thus be increased as a whole.

In a further development, the evaluation unit 1 can activate a device or receiving device, which are not shown, when the occurrence of an event is determined, in particular a household appliance, preferably a kitchen appliance, a milk bottle heater or an oven. If the event is the awakening or forecasted awakening of an infant, the alerted parent can then find, at a respective device, a bottle of milk or an amount of baby food in an already running process of its preparation or in a finished (prepared) state. The infant can thus be fed more quickly. At the same time, the time of interruption of the resting phase of the alerted parent is reduced.

As described above, the system is configured in such a way that all persons 2, 3 whose measured vital parameter reaches a threshold or exceed a threshold are selected. If the evaluation based on the measured vital parameters shows that several persons are suitable for alerting, all these several persons of the plurality of persons can thus be selected and alerted. If always all selected persons are alerted, the risk is reduced that no one of the alerted persons has taken notice of the alerting. In one embodiment, an alerted person receives an information about all other selected and/or alerted persons on the display 14, 15 of the alert unit. In one embodiment, an alerted person can send a message to one or all other selected and/or alerted persons. Preferably, the message indicates that the sender is currently busy or unavailable. Alternatively or complementary, the message may indicate that the sender is taking care of the event, which was indicated by the alert, and that the other alerted persons are not needed.

In one embodiment, the system comprises an alert unit 12, 13 for each person 2, 3. In one embodiment, the alert unit 12, 13 and/or the evaluation unit 1 can establish a data connection to a kitchen appliance (food processor) or a robot vacuum cleaner and/or control them. A person, who has just been alerted, can thus control the kitchen appliance for preparing food or the robot vacuum cleaner for changing a cleaning plan without any loss of time through the alert unit, e.g. from the bed. In particular, said control includes activating a predefined action, e.g. deactivating the robot vacuum cleaner or triggering an automatic food preparation by the kitchen appliance.

In the variant with the kitchen appliance, this enables the alerted person to remain in bed for a few minutes while the kitchen appliance automatically prepares the food. These few minutes in bed, however, significantly reduce the stress of getting up, because it gives the circulation, body and head the opportunity to slowly move from a rest condition to an active condition.

In particular, the display 14, 15 of the alert unit shows an information about the current status of the food preparation by the kitchen appliance, the recipe currently being processed and/or a control command from evaluation unit 1 to the kitchen appliance. The stress can thereby be further reduced. Preferably, the alert unit can be used to select a recipe or a food (dishes) for automatic preparation. Preferably, the recipes or respective food (dishes) are then displayed with the planned preparation time (duration).

In particular, a cleaning plan is provided for the robot vacuum cleaner. Preferably, the cleaning plan includes a driving route and/or a cleaning schedule. For example, the schedule defines that the robot vacuum cleaner regularly travels along the driving route to clean the floor of living areas.

In the variant with the robot vacuum cleaner and its data connection and/or control through the alert unit, it is enabled that the alerted person can change the cleaning plan promptly and on the spot (from the present location) based on the event of which the person took notice from by the alert. When, for example, a baby wakes up at night, the cleaning plan can be immediately changed by the alert unit so that the robot vacuum cleaner is promptly deactivated, that the children's room is not approached (change of route), or the route is driven in a timely delayed manner (change of schedule). Especially for babies, this is an essential advantage for the following reasons. Because robots vacuum cleaner are dangerous for babies on the floor and because the operating noises usually do not wake up sleeping babies, robot vacuum cleaners are usually programmed to clean at night. However, a waking baby is put into a higher state of activity by the sounds and/or the sight of a moving robot vacuum cleaner, which puts an actually tired baby into a higher waking state, from which it is much more difficult and exhaustive to bring the baby back to sleep. This can be prevented by the embodiment as described above, so that the alerted person does not have to get up abruptly and run to the robot vacuum cleaner, but can remain in bed for a short time until the circulation, the body and the head have adapted to the forthcoming getting up, for example at night due to the awakened baby. The stress can thus be significantly reduced through this embodiment.

In particular, an information about the current status of the robot vacuum cleaner, the cleaning plan and/or a control command from evaluation unit 1 to the robot vacuum cleaner is displayed on the display 14, 15 of the alert unit. Stress can thereby be further reduced.

A kitchen appliance has at least the three functions of heating, chopping and blending a food. Preferably, the kitchen appliance can access stored recipes for a variety of foods. Preferably, a recipe can be displayed on the kitchen appliance via an interactive display, e.g. touch screen display, and processed by the user step by step. In one embodiment, the kitchen appliance can process a recipe completely self-acting and thus automatically prepare a food.

The invention claimed is:

1. A system for alerting a person or persons, the system comprising
an evaluation unit configured to determine an occurrence of an event and, when the event occurs, to alert a plurality of persons so as to inform them about the occurred event,
wherein the system includes for each person a control unit and a sensor, wherein the control unit is configured to be connected to the evaluation unit for exchanging data, and the sensor is configured to measure a vital parameter of the respective person that is communicated to the evaluation unit, and
wherein the system is configured such that when the evaluation unit determines the occurrence of an event, at least one person of the plurality of persons is selected based on the measured vital parameters and only the at least one selected person can be alerted, wherein the evaluation unit is configured to compare the measured vital parameters of the individual persons with each other in order to select the at least one person.

2. The system of claim 1, wherein the system is configured such that all persons are selected whose measured vital parameter reaches a threshold or exceeds a threshold.

3. The system of claim 1, wherein the system provides an alert unit for each person that coupled for communication with the evaluation unit and is configured to provide an alert about the occurred event.

4. The system of claim 1, wherein the system includes a display for each person coupled for communication with the evaluation unit and configured to display information about the occurred event about which the person was informed.

5. The system of claim 1, wherein the control unit and the sensor are integrated in a receiving device sized to be carried by the respective person.

6. The system of claim 5, wherein an alert unit and/or a display are integrated in the receiving device.

7. The system of one of claim 5, wherein the receiving device has a fastening means for fastening to the body of a person or comprises a skin-compatible contact surface for direct fastening to the body.

8. The system of claim 5, wherein the receiving device is a bracelet, a footband or a headband.

9. The system of claim 1, wherein at least one of the sensor and an alert unit are configured for direct skin contact.

10. The system of claim 1, wherein an alert unit included in a receiving device that communicates with the evaluation unit is a vibration generator.

11. The system of claim 1, wherein the evaluation unit compares the measured vital parameters with a threshold in order to select the at least one person.

12. The system of claim 1, wherein the evaluation unit is equipped with a machine learning algorithm for selecting the at least one person.

13. The system of claim 1, wherein the sensor is a gyrometer.

14. The system of claim 1, wherein the system is configured such that the person with the least tension is alerted.

15. The system of claim 14, wherein blood pressure, pulse frequency and/or activity is used as vital parameter.

16. The system of claim 1, wherein the system is configured such that the person with the least tension is alerted amongst awake persons and the person who is in a sleep phase with the least depth of sleep is selected amongst sleeping persons, wherein a number of changes of direction per time interval is determined for determining a sleep phase or a waking state.

17. A method of using a system for alerting a person or persons, the method comprising
determining an occurrence of an event by an evaluation unit,
measuring vital parameters from a plurality of persons by a sensor,
selecting at least one of the plurality of persons to alert of the event based on the measured vital parameters, wherein the step of selecting includes comparing the measured vital parameters of the individual persons with each other by the evaluation unit, and
alerting the selected at least one of the plurality of persons.

18. The method of claim 17, wherein the event determined is awakening of an infant.

19. The method of claim 17, wherein the plurality of persons are parents of the infant and only one of the parents are alerted.

20. The method of claim 17, wherein the event is an incoming telephone call, an incoming service request, in particular for persons on standby duty, or a message from a monitoring device such as a burglar alarm system or an audio baby monitor.

* * * * *